United States Patent [19]
Suzuki et al.

[11] Patent Number: 6,013,065
[45] Date of Patent: Jan. 11, 2000

[54] ABSORBENT ARTICLE INCLUDING FIRST AND SECOND APERTURES AND ELASTIC MEMBERS

[75] Inventors: Migaku Suzuki, Kanagawa; Hiroaki Fukui, Saitama, both of Japan

[73] Assignee: Paragon Trade Brands, Norcross, Ga.

[21] Appl. No.: 09/134,814

[22] Filed: Aug. 17, 1998

Related U.S. Application Data

[60] Division of application No. 08/674,815, Jul. 3, 1996, Pat. No. 5,830,203, which is a continuation-in-part of application No. 08/248,423, May 24, 1994, abandoned.

[51] Int. Cl.⁷ .................................................. A61F 13/15
[52] U.S. Cl. ...................... 604/385.2; 604/385.1
[58] Field of Search .................. 604/385.1–386, 604/393, 394, 396, 378

[56] References Cited

U.S. PATENT DOCUMENTS

| | | | |
|---|---|---|---|
| 4,892,536 | 1/1990 | DesMarais et al. | 604/385.2 |
| 5,213,645 | 5/1993 | Nomura et al. | 156/164 |
| 5,269,775 | 12/1993 | Freeland et al. | 604/385.1 |
| 5,397,316 | 3/1995 | LaVon et al. | 604/378 |
| 5,830,203 | 11/1998 | Suzuki et al. | 604/385.2 |
| 5,836,931 | 11/1998 | Toyoda et al. | 604/385.2 |

FOREIGN PATENT DOCUMENTS

| | | | |
|---|---|---|---|
| 3186261 | 8/1991 | Japan | 604/385.2 |
| 5-42180 | 2/1993 | Japan. | |
| 5-76567 | 3/1993 | Japan. | |
| 5-285168 | 11/1993 | Japan | 604/385.2 |
| 2022026 | 11/1991 | Spain. | |
| 2268073 | 1/1994 | United Kingdom | 604/385.1 |
| 2276529 | 10/1994 | United Kingdom. | |
| 9620674 | 7/1996 | WIPO | 604/385.2 |

*Primary Examiner*—Mark O. Polutta
*Attorney, Agent, or Firm*—Hunton & Williams

[57] ABSTRACT

An absorbent article incorporating a main body which has a waist hole and a pair of leg holes, and comprises a topsheet positioned in a facing relation to a wearer's body, a backsheet positioned opposite thereto, and an absorbent core interposed between the backsheet and the topsheet. The topsheet is a composite which comprises two layers of sheet material and two elastic members sandwiched between the two sheets of material. The topsheet further has communicating means disposed in a crotch region of the absorbent article for receiving body exudates. The communicating means is surrounded by the elastic members which form leg gathers, and serves as a passage to communicate body exudates to a space defined between the topsheet and the backsheet. The absorbent article of the present invention can provide excellent flexibility, a snug fit and comfort to a wearer during use, while effectively preventing leakage from the leg gathers.

19 Claims, 9 Drawing Sheets

ABSORBENT ARTICLE INCLUDING FIRST AND SECOND APERTURES AND ELASTIC MEMBERS

This application is a divisional application of U.S. patent application Ser. No. 08/674,815, filed Jul. 3, 1996, now U.S. Pat. No. 5,830,203 which is a continuation-in-part of application Ser. No. 08/248,423, filed May 24, 1994 now abandoned.

FIELD OF THE INVENTION

The present invention relates to a pant-type absorbent article (such as those often referred to as "tapeless-type" or "training pant type") which includes a pair of leg holes for leg insertion, and a waist hole for encircling a waist portion of a body. The present invention further relates to a method for manufacturing such an absorbent article. The absorbent article of this type may be used for infant and adult diapers, feminine sanitary products and the like.

SUMMARY OF THE INVENTION

Absorbent articles, particularly infant and adult diapers have recently gained increased acceptance from consumers for their advantageous characteristics of stability during use and reduced leakage.

In order for the tapeless absorbent articles to fully exhibit their advantageous characteristics, they need to snugly fit to a user's body, particularly at leg hole portions thereof. To this end, such tapeless absorbent articles have elastically stretchable ruffles or leg gathers, as they are generally called, along peripheries of the leg holes. The absorbent articles also have top and back sheets and an absorbent core sandwiched therebetween.

One example of such tapeless absorbent articles with leg gathers is disclosed in Japanese Patent Application No. 3-195558. Two sets of elastic members are attached along the peripheries of the leg holes to form leg gathers. Each set of elastic members extends along one leg hole from a front end of the leg hole to a midpoint of the leg hole, and continuously extends transversely of a central region (crotch region) of the article to a midpoint of the other leg to form a cross-over portion. From the midpoint of the other leg hole, each set of elastic members further extends therealong to a rear end of the other leg hole. Those two sets of elastic members are arranged so as to define a somewhat X-shaped configuration.

Such arrangement of the elastic members advantageously facilitates a continuous manufacturing process of the absorbent articles. Specifically, a liquid impermeable sheet in a continuous web form is continuously transported in one direction. Continuous elastic strands are fed onto the sheet in a sinusoidal configuration for securement thereto. The resultant combination is cut at a predetermined interval to form a composite backsheet incorporating the elastic members secured thereto.

The elastic members arranged along peripheries of the leg holes in the aforementioned, conventional tapeless absorbent article function to form leg gathers therealong. However, the elastic members extending transversely of the crotch region not only are non-functional waste material but cause the crotch region of the absorbent article to elastically stretch and contract, thereby excessively pressing against a wearer's body. Such elastic action impairs flexibility and softness in the crotch region which are the properties desired in providing comfort to the wearer during use.

One drawback of conventional tapeless absorbent articles is urine leakage from sides of the articles. Another major drawback thereof is a poor isolation or containment of fecal material. Particularly, in the above-discussed tapeless absorbent article incorporating the two sets of elastic members which traverse the crotch region thereof, those elastic members urge the crotch region into excessively tight contact with the wearer's body. Such article design has a poor fecal material containment. Fecal material containment is especially poor when elastic members are bonded to the backsheet of the article, such as disclosed in Japanese Patent Application No. 3-241957, to Akagi. Such a configuration causes the elastic members to urge the absorbent core into contact with the wearer's body, which may cause diaper rash or other skin irritation. Additionally, having elastic members bonded to the backsheet squeezes the absorbent core between the backsheet and the wearer's body, reducing the core's ability to absorb excreted material.

It is an object of the present invention to provide an improved absorbent article which is capable of eliminating the above-described disadvantages that conventional articles possess, so that any undesirable deformation of the crotch region due to the contracting force of the elastic members can be avoided, and the effective containment of fecal material in the crotch region is insured.

In accordance with the present invention, there is provided an absorbent article which is provided with a main body having a waist hole and a pair of leg holes. The main body comprises a liquid impermeable backsheet, a liquid permeable topsheet and an absorbent core interposed between the backsheet and the topsheet. The absorbent article is further provided with a waist gather disposed along the waist hole, and a leg gather disposed along each of the pair of leg holes.

The topsheet includes two layers of sheet material, and two elastic members interposed between the two sheets of material to form a composite topsheet. Because the elastic members are not bonded to the backsheet, the absorbent core is held more loosely and is able to retain more liquids. The topsheet further includes communicating means formed so as to penetrate through said sheet material.

The two elastic members extend along a periphery of one of the leg holes from one end thereof into a midpoint thereof, and continuously extend therefrom along a periphery of the communicating means to a midpoint of the other leg hole. From the midpoint, each elastic member extends to one end of the other leg hole, so that each elastic member is arranged to define a U-shaped configuration.

In accordance with the absorbent article of the present invention, the topsheet has the communicating means located in the crotch region of the absorbent article. The elastic members are disposed to extend along the periphery of the communicating means to form the leg gathers. The communicating means serves as an inlet for a pocket defined between the topsheet and the backsheet for receiving urine and fecal material. This provides comfort to a wearer during use. Furthermore, the arrangement of a part or all of the elastic members which form the leg gathers along the periphery of the communicating means can help provide shape and positional stability of the pocket communicating means, which provides further comfort to the wearer during use.

The elastic members which form the leg gathers are disposed to extend primarily around the leg holes, and are not located in the crotch region where elastic members are not required to be present. Accordingly, the absorbent article has softness and flexibility, and provides a snug fit and comfort to the wearer during use, with its leg gathers effectively preventing leakage from the article. Furthermore, as the elastic members are not bonded to the backsheet, they are not viewed or observed from outside the article. This helps provide the article with a good appearance in its crotch region.

One embodiment of the present invention will be explained hereinafter with reference to the drawings.

DESCRIPTION OF THE PREFERRED EMBODIMENT

Figure 1:
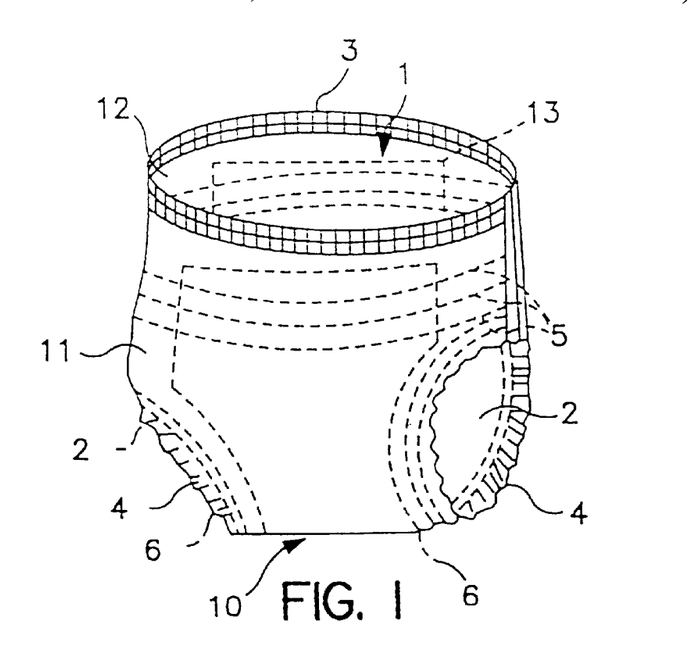
FIG. 1 is a perspective view illustrating one embodiment of an absorbent article in accordance with the present invention.
Figure 2:
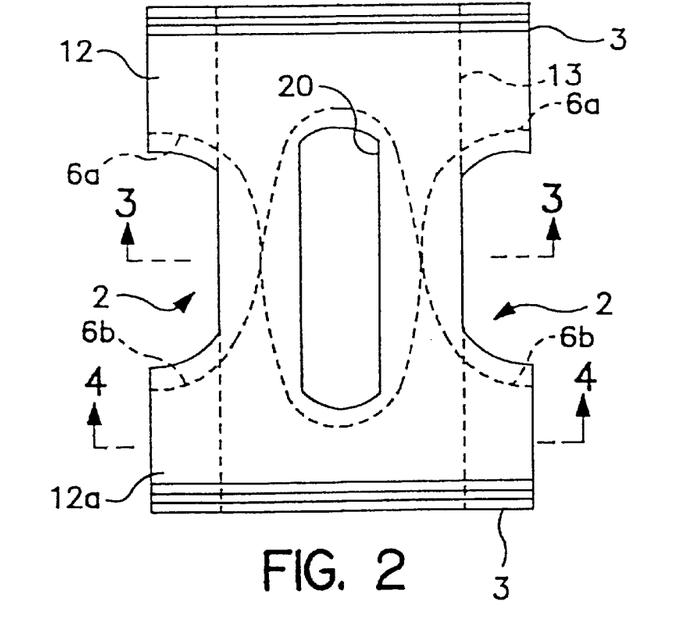
FIG. 2 is a developed plan view of the absorbent article of FIG. 1.

FIG. 1 is a perspective view illustrating one embodiment of a tapeless absorbent article in accordance with the present invention. FIG. 2 is a plan view illustrating the absorbent article of FIG. 1 prior to folding and sealing the respective side panels thereof to each other.

The absorbent article as illustrated in FIG. 1 comprises a main body 10 of a pant-type which has a waist hole 1 and a pair of leg holes 2. The main body 10 includes a waist gather 3 disposed along the periphery of the waist hole 1, and a leg gather 4 disposed along the periphery of each of the leg holes 2. The leg gather 4 is formed by the contracting force of a number of elastic members 6 incorporated therein. A reference numeral 5 indicates elastic members optionally provided for improved fitting of the main body to a waist portion of a wearer.

The main body 10 comprises a backsheet 11 formed of liquid impermeable material, a topsheet 12 formed of liquid impermeable material, preferably hydrophobic material, and an absorbent core 13 interposed therebetween.

Figure 3:
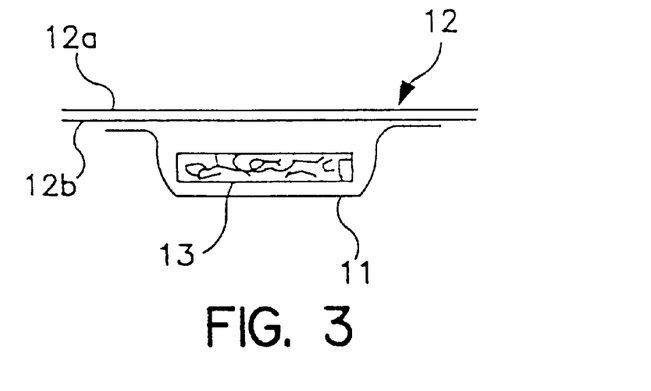
FIG. 3 is a cross-sectional view taken along a line A—A of FIG. 2.
Figure 4:
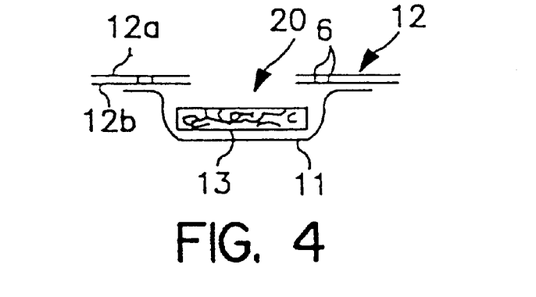
FIG. 4 is a cross-sectional view taken along a line B—B of FIG. 2.
Figure 5:
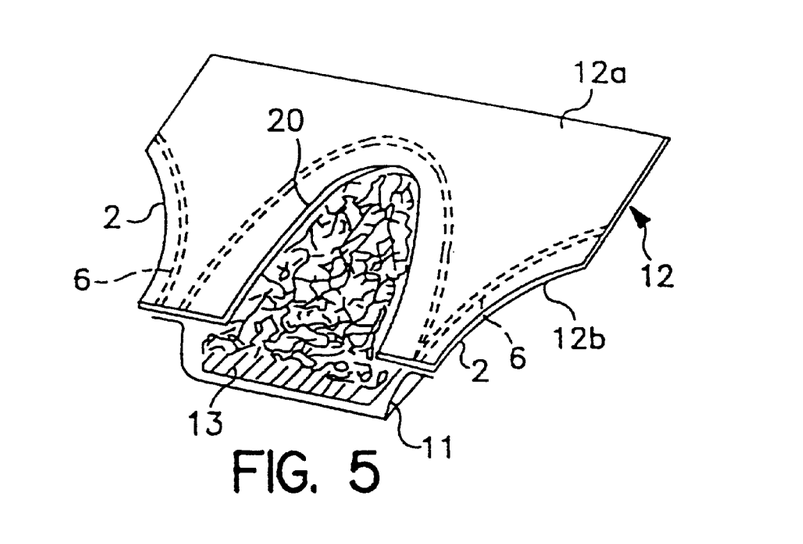
FIG. 5 is a fragmentary enlarged, perspective view of the absorbent article of FIG. 1.

As illustrated in FIGS. 3 through 5, the topsheet 12 comprises a first layer 12a positioned in facing relation to a wearer's body, and a second layer 12b positioned in facing relation to the backsheet 11. A communicating means, such as a through aperture 20 is disposed in a crotch area of the garment located between the pair of leg holes 2.

In the illustrated embodiment, the elastic members 6 extend inwardly of and along right and left contoured edges of the absorbent article to form the pair of right and left leg gathers 4, and comprise separate, first and second elastic members 6a, 6b.

The elastic members 6 generally comprise a number of parallel rubber threads, or strands, to form a leg gather that is flexible and has sufficient elastic contractibility to provide leakage protection. Each elastic member 6a, 6b can generally be considered a unitary and integral group of rubber threads, although particular designs may separate an elastic member into separate rubber threads.

In the illustrated example, the first elastic member 6a meets or crosses the second elastic member 6b at a midpoint of one of the leg holes 2, and continuously extends therefrom along a half peripheral portion of the aperture 20 to a midpoint of the other of the leg holes 2. From the midpoint, the first elastic member 6a further extends to one end of the other of the leg holes 2. The second elastic member 6b is disposed to extend like the first elastic member 6a, but with its orientation being reversed therefrom. The first and second elastic members 6a, 6b are bonded in sandwiched relationship between the first and second layers 12a, 12b.

Explaining further, the first elastic member 6a extends along a periphery of a first leg hole from the first end thereof to a midpoint thereof, continuously extends therefrom along one portion of the periphery of the communicating means, or aperture, 20 to a midpoint of a second leg hole, and further extends therefrom to the first end of the second leg hole so that the first elastic member is disposed in a first substantially U-shaped configuration. The second elastic member 6b extends along a periphery of the first leg hole from the second end thereof to a midpoint thereof, continuously extends therefrom along a portion of the periphery of the communicating means, or aperture, 20 to a midpoint of the second leg hole and further extends therefrom to the second end of the second leg hole so that the second elastic member is disposed in a second substantially U-shaped configuration which is inverted relative to the first U-shaped configuration described previously.

The first and second elastic members each form one half of a leg gather on each leg hole and extend around one half the periphery of the aperture. Together, the elastic members form both leg gathers and encircle the aperture.

The embodiment of FIG. 2, consequently, only requires two unitary elastic members to form both the crotch and leg gathers. This construction is more efficient and economical to manufacture than previously known constructions of tapeless absorbent articles that require at least three elastic members to form a similar pair of U-shaped patterns inverted relative to each other.

The composite sheet of such construction can be readily manufactured by the following process.

Figure 6:
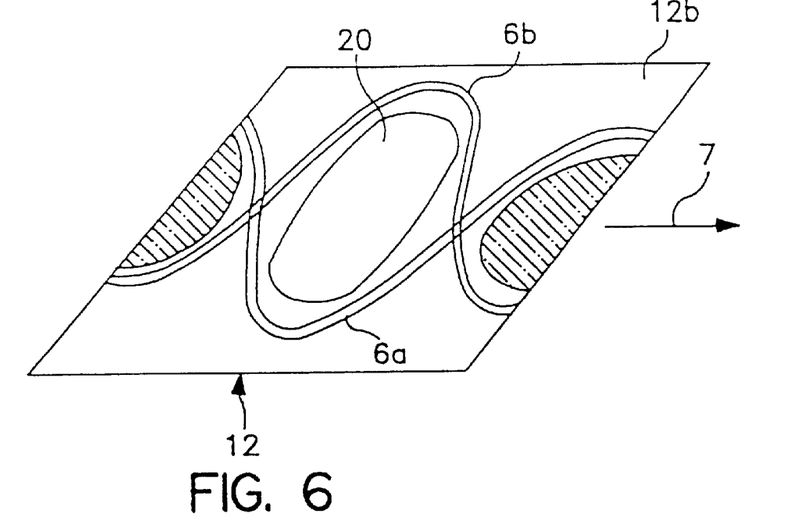
FIG. 6 is a perspective view illustrating the positional relationship of a topsheet and elastic members incorporated in the absorbent article.

Elongated sheet material in web form that forms the second layer 12b is continuously transported in one direction, as illustrated by arrow 7 in FIG. 6. The two elastic members 6a, 6b are placed onto the sheet material 12b in overlapping sinusoidal configurations with an inverted phase relation to each other. A second sheet of material 12a (not shown in FIG. 6) is further overlaid onto the sheet material 12b so as to sandwich the elastic members therebetween. The second sheet of material 12a and the elastic members are bonded to the sheet material 12b by conventional bonding means to form a composite sheet. The through aperture 20 is simultaneously formed which penetrates the dual-layered sheet material. The resultant composite topsheet is then cut into an individual, article unit length which is further cut to form leg holes (shown by cross hatch lines).

The composite sheet thus formed is subsequently combined with the backsheet 11, the absorbent core 13, and the other article elements to manufacture the absorbent articles in accordance with conventional manufacturing processes. The relative positions of the layered materials within the garment are illustrated in the cross-sectional views FIGS. 3–5.

Figure 7:
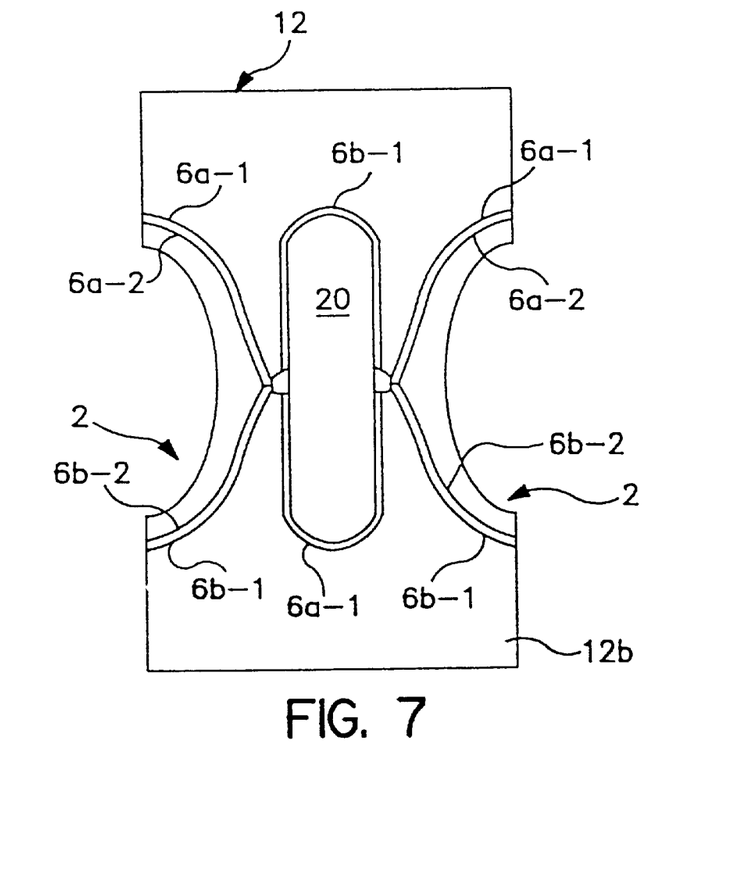
FIG. 7 is a developed, plan view illustrating a topsheet incorporated in a second embodiment of the absorbent article in accordance with the present invention.

In the embodiment as shown in FIG. 7, first and second elastic members 6a, 6b are disposed to extend along peripheries of the leg holes 2. In this case, two rubber threads $6_{a-1}$, $6_{a-2}$ follow closely parallel paths, and two rubber threads $6_{b-1}$, $6_{b-2}$ follow closely parallel paths. The rubber threads $6_{a-1}$, $6_{b-1}$, which are positioned more remote from the peripheries of the leg holes 2 extend between the pair of leg holes 2 along the periphery of the aperture 20. However, the rubber threads $6_{a-2}$, $6_{b-2}$ which are positioned closer to the peripheries of the leg holes 2 are discontinued at the periphery of the aperture 20 by cutting.

In such construction, the contracting force of the elastic members 6 along the periphery of the aperture 20 is controlled to be smaller than that along the peripheries of the leg holes 2, so that the inlet of the pocket provided by the aperture 20 may not be excessively restricted or closed. The contracting forces along the periphery of the aperture 20 and along the peripheries of the leg holes 2 can be selectively controlled by setting a ratio of the number of rubber threads which form the elastic members 6 to the number of rubber threads which are severed adjacent the periphery of the aperture 20 within a proper range.

Figure 8:
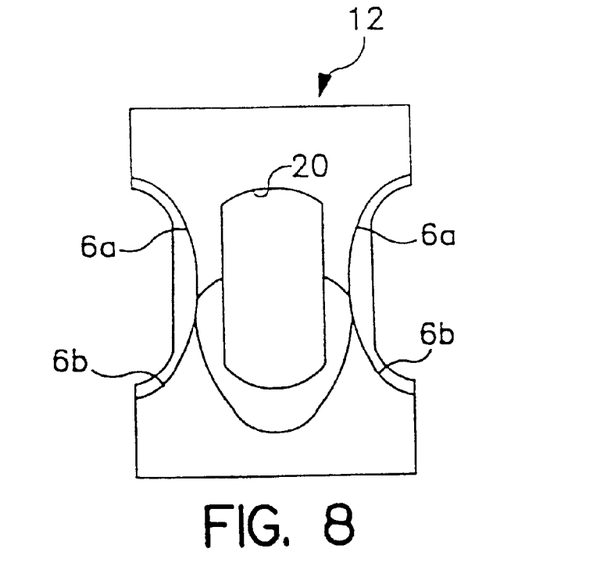
FIG. 8 is a developed, plan view illustrating a topsheet incorporated in a third embodiment of the absorbent article in accordance with the present invention.

FIG. 8 illustrates the topsheet 12 in still another embodiment of the absorbent article in accordance with the present invention. In this embodiment, the first elastic member 6a extends along the periphery of the aperture 20 while the second elastic member 6b is discontinued at the periphery of the aperture 20 by cutting.

Figure 9:
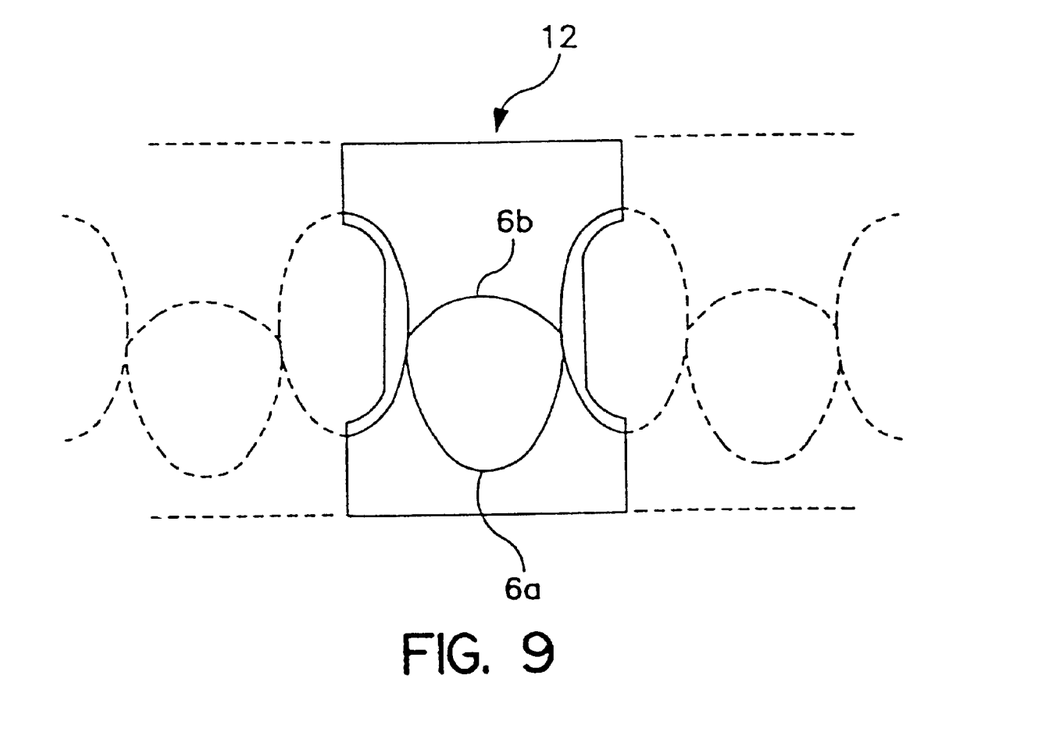
FIG. 9 is an explanatory view illustrating the positional relationship of sheet materials and elastic members during a process of manufacturing the topsheet of FIG. 8.

The topsheet 12 of such construction can be readily manufactured by a continuous process. Typically, during the process that the two elastic members 6a, 6b are positioned between the two sheet materials in continuous web forms for attachment thereto, the amplitude of the sinusoidal configuration that the first elastic member 6a describes is set greater, and the amplitude of the sinusoidal configuration that the second elastic member 6b describes is set smaller, as illustrated in FIG. 9. The aperture 20 is formed in the sheet material by cutting which simultaneously splits the second elastic member 6b at a periphery of the aperture as shown.

Figure 10:
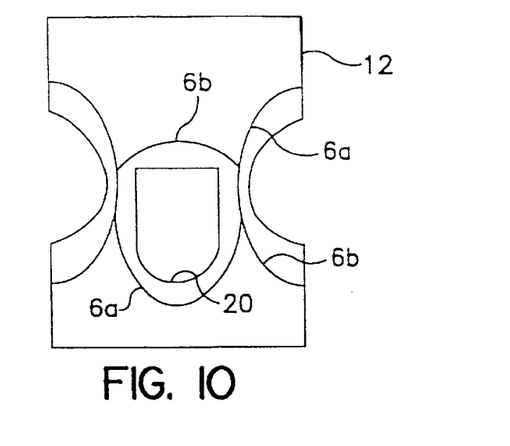
FIG. 10 is a developed, plan view illustrating a topsheet incorporated in a fourth embodiment of the absorbent article in accordance with the present invention.

FIG. 10 illustrates a fourth embodiment of the absorbent article wherein the aperture 20 is formed within an area surrounded by the two elastic members 6a, 6b in a crotch region of the topsheet 12 as illustrated in FIG. 9.

Figure 11:
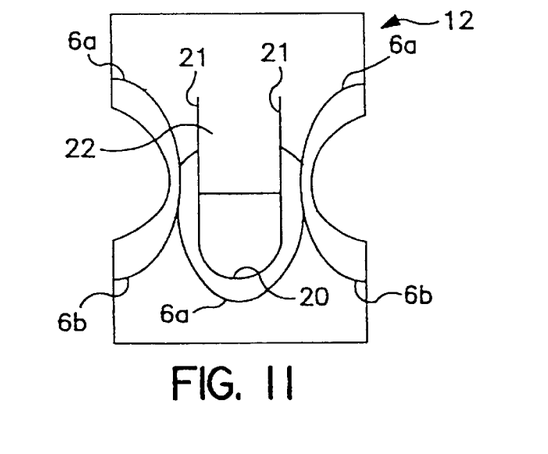
FIG. 11 is a developed, plan view illustrating a topsheet incorporated in a fifth embodiment of the absorbent article in accordance with the present invention.
Figure 12:
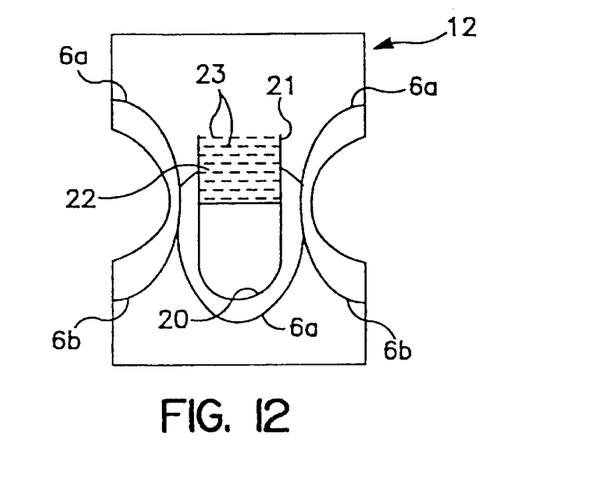
FIG. 12 is a developed, plan view illustrating a topsheet incorporated in a sixth embodiment of the absorbent article in accordance with the present invention.

FIG. 11 illustrates a fifth embodiment of the absorbent article which incorporates slits 21 extending from respective sides of the aperture 20 to form a flap 22 in the topsheet 12 of FIG. 10. A number of slits 23 may be additionally placed in the flap 22 in accordance with a sixth embodiment of the absorbent article as illustrated in FIG. 12.

Figure 13:
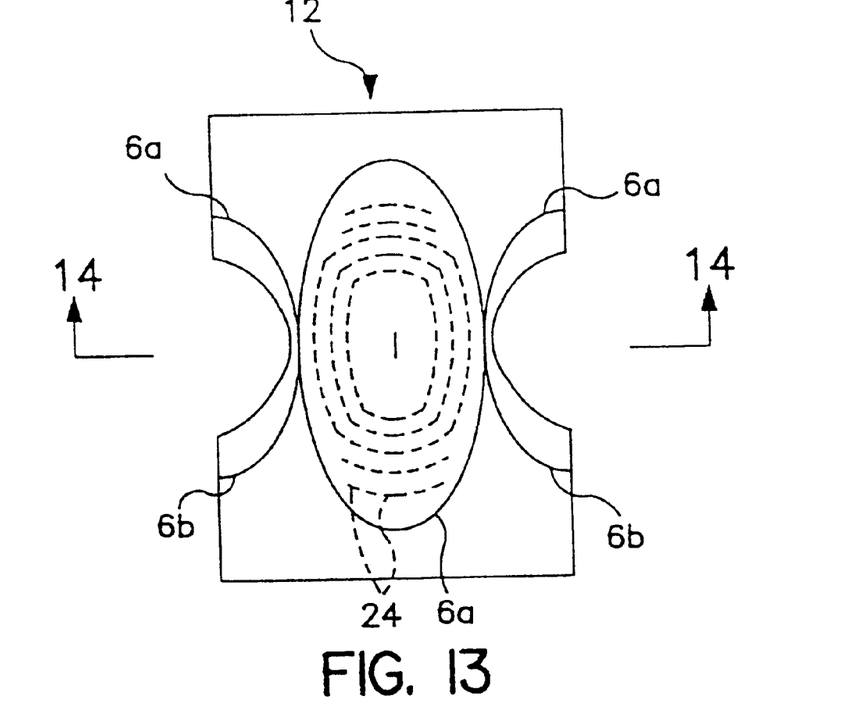
FIG. 13 is a developed, plan view illustrating a topsheet incorporated in a seventh embodiment of the absorbent article in accordance with the present invention.
Figure 14:
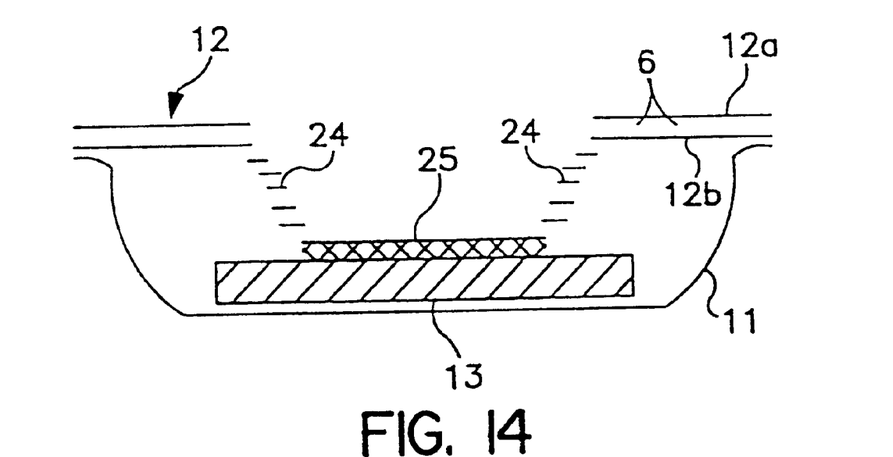
FIG. 14 is an enlarged, cross-sectional view taken along a line C—C of FIG. 13.

FIGS. 13 and 14 illustrate the topsheet 12 incorporated in a seventh embodiment of the absorbent article. In this embodiment, the two elastic members 6a, 6b define a substantially oblong crotch area, and a number of slits 24 are formed within and along a periphery of the area. Those slits 24 permit variation in the elevation of a central area 25 surrounded by the slits in a thickness direction of the topsheet 12 as the slits 24 open up. More specifically, the slits 24 provide an accordion-like characteristic and allow a central portion of the topsheet attached to the absorbent core to remain closely adjacent the central area of the absorbent core as the core shifts toward and away from the user. The central area of the topsheet is bonded to the absorbent core 13 by appropriate bonding means such as hot-melt-type adhesives.

Accordingly, the topsheet 12 defines a recess in the crotch region of the article which serves as a pocket for receiving and containing body wastes.

Figure 15:
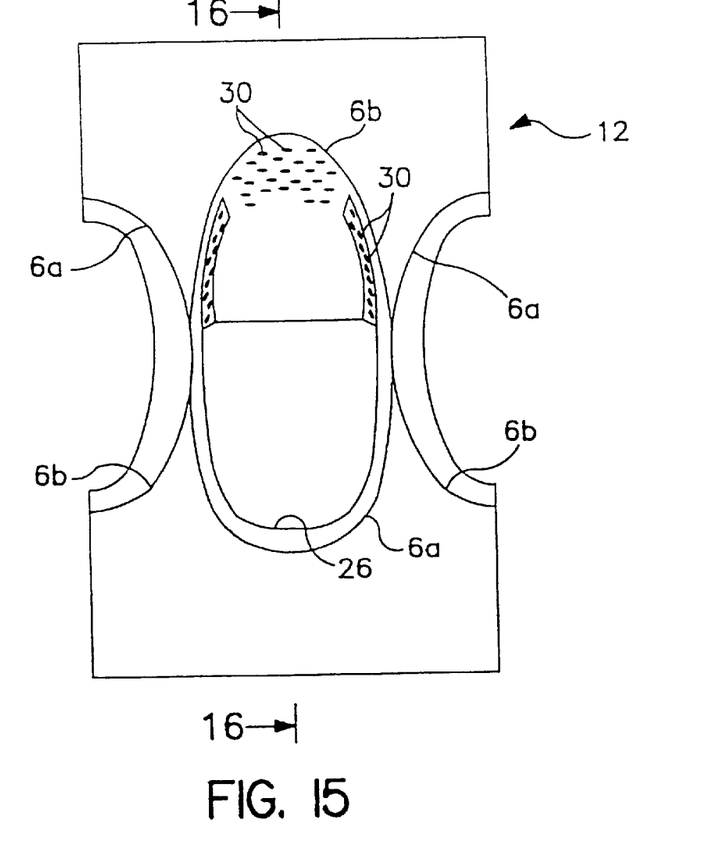
FIG. 15 is a developed, plan view illustrating a topsheet incorporated in a eighth embodiment of the absorbent article in accordance with the present invention.
Figure 16:
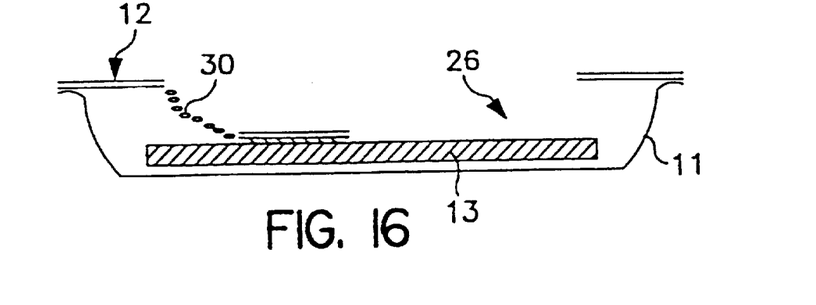
FIG. 16 is a cross-sectional view taken along a line D—D of FIG. 15.

FIGS. 15 and 16 illustrate an eighth embodiment of the absorbent article wherein about a half part of the substantially oblong crotch region as shown in FIG. 13 is cut out to form an aperture 26. The aperture 26 is positioned in a rear section of the absorbent article in use so as to serve as a pocket of high containment capacity for receiving and containing body wastes, particularly fecal material. Like the slits 24 in FIG. 14, slits 30 formed in the front section of the topsheet permit at least a portion of the topsheet to remain closely adjacent the core 13 and shift therewith toward and away from the user. Explaining further, as a portion of the topsheet in FIG. 14 is secured closely adjacent the absorbent core in the central area 25 to rise and fall therewith, so too is a portion of topsheet 12 in Figures. 15 and 16 attached closely adjacent the core 13. The backsheet and absorbent core area are not pressed tightly toward the user and are spaced apart from the user in the central area. In this position, slits 30 are opened up to allow a portion of topsheet 12 to remain closely adjacent the absorbent core. If the core is urged toward the user, the slits close up. The slits, therefore, provide an accordion-like characteristic that allow the portion of the topsheet adjacent the core to closely follow movement of the core.

Figure 17:
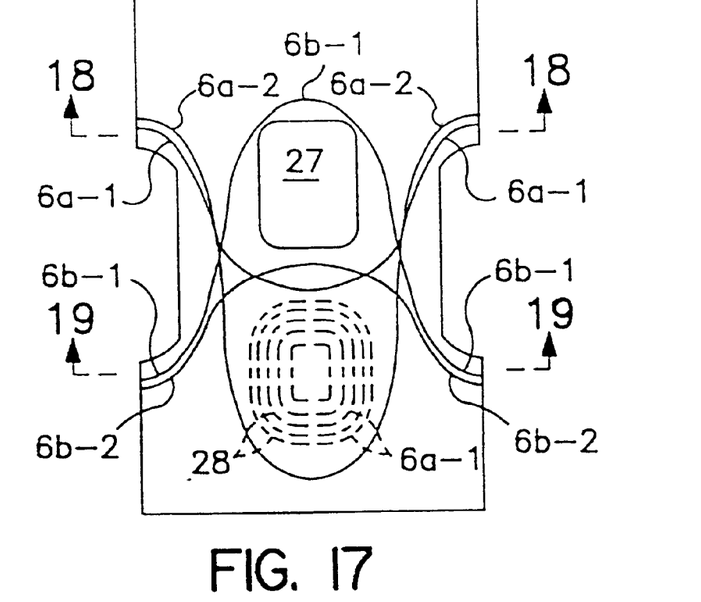
FIG. 17 is a developed, plan view illustrating a topsheet incorporated in a ninth embodiment of the absorbent article in accordance with the present invention.
Figure 18:
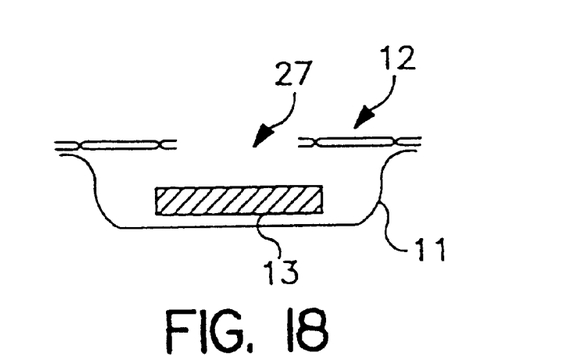
FIG. 18 is a cross-sectional view taken along a line E—E of FIG. 17.
Figure 19:
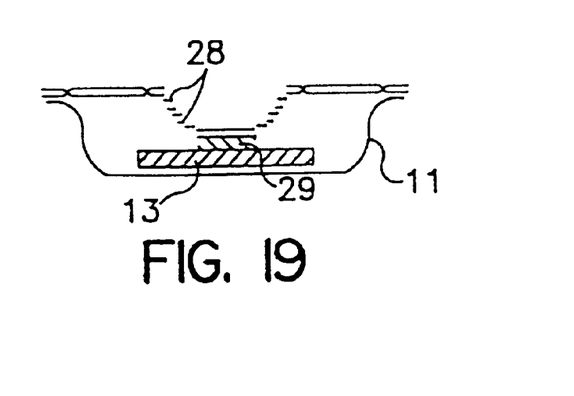
FIG. 19 is a cross-sectional view taken along a line F—F of FIG. 17.

FIGS. 17 through 19 illustrate a ninth embodiment of the absorbent article in accordance with the present invention. The first and second elastic members 6a, 6b respectively comprise first, two rubber threads $6_{a-1}$, $6_{a-2}$, and second, two rubber threads $6_{b-1}$, $6_{b-2}$. The rubber threads $6_{a-1}$, $6_{b-1}$ are disposed to extend outwardly of and along the substantially oblong, crotch region, while the rubber threads $6_{a-2}$, $6_{b-2}$ are disposed to extend transversely of a central portion of the crotch region. Accordingly, the crotch region is divided into a pair of first and second regions which are respectively surrounded by rubber threads. The first region includes an aperture 27, and the second region includes a number of slits 28 arranged in a number of circles. A topsheet portion surrounded by the slits 28 is bonded onto the absorbent core 13 by hot-melt-type adhesives 29, so that a recess is defined in the absorbent article. The rubber threads $6_{a-2}$ and $6_{b-2}$ cross between and separate the first region from the second region. A mixture of urine and fecal matter increases the likelihood of skin irritation when contacting a wearer's skin. Thus, it is advantageous to separate urine from fecal matter. Having separate apertures in the first and second regions disposes of urine and fecal matter separately. The rubber threads $6_{a-2}$ and $6_{b-2}$ further aid in such separation by elevating the topsheet between the first and second region to contact the wearer's skin and impede the flow of urine between the regions. FIG. 19 shows that the second region defines an aperture therein that tapers as it approaches the absorbent core 13 to funnel urine into the desired region of the absorbent core. This further ensures separation between urine and fecal matter.

Figure 20:
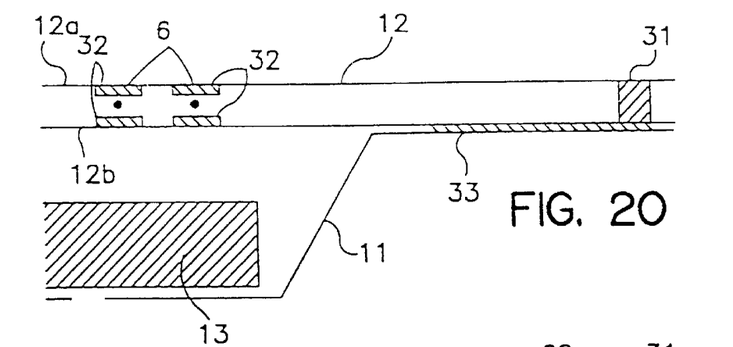
FIGS. 20 to 23 illustrate other absorbent articles embodying the present invention in cross section to reveal the structure of a portion of the leg gather at one side of an article.

The absorbent article shown in FIG. 20 comprises a pair of sheets of material 12a and 12b joined together by means of a layer 31 of a hot-melt-type adhesive, and an absorbent core 13. Elastic members 6 are sandwiched between the members 12a and 12b of the topsheet 12 and bonded thereto by hot-melt-type adhesive layers 32. Numeral 33 depicts a layer of hot-melt-type adhesive provided for bonding the backsheet and topsheet. In this embodiment, the elastic members 6 are not connected to the backsheet 11. Prior absorbent articles have had the elastic members connected to the backsheet below the absorbent core. Such a configuration results in the elastic members pushing the absorbent core into the wearer's body during use, which may cause skin irritations and reduces the absorbing potential of the absorbent core. By securing the elastic members to the topsheet and not the backsheet in the crotch region, the absorbent core is positioned away from the wearer's body. Additionally, the absorbent core is loosely held within the garment to allow for maximum absorption.

The foregoing description has related to an absorbent article in which the topsheet has a dual-layered construction. This has an advantage in production because the elastic members may easily be held between the two layers. However, the present invention allows the use of a topsheet of single layer material, if the elastic members can be suitably secured on the topsheet. Explaining further, because the tension in the portions of the elastic members surrounding the central aperture may be less than that surrounding the leg holes, it is possible to secure them to the topsheet by an adhesive, while the portions surrounding the leg holes are supported by the backsheet.

Figure 21:
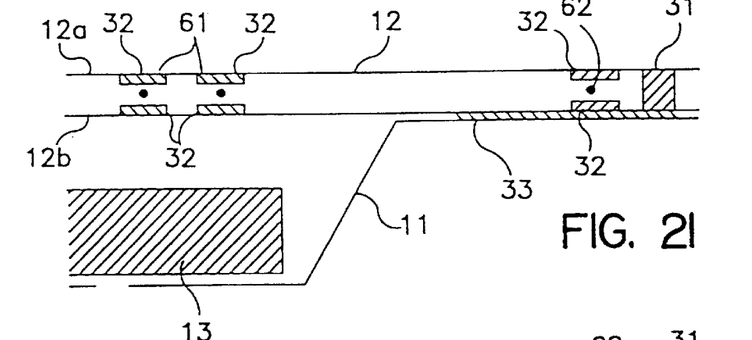

In the embodiment shown in FIG. 21, inner elastic member 61 and outer elastic member 62 are disposed between a pair of materials 12a and 12b constituting a topsheet 12, the materials 12a and 12b being joined together by means of a layer of an adhesive 31. The outer elastic member 62 is connected to the backsheet 11 by adhesive 32, while the inner elastic members 61 are not connected to the backsheet. A portion of the topsheet 12 is secured to the backsheet 11 by a layer 33 of a hot-melt-type adhesive.

Figure 22:
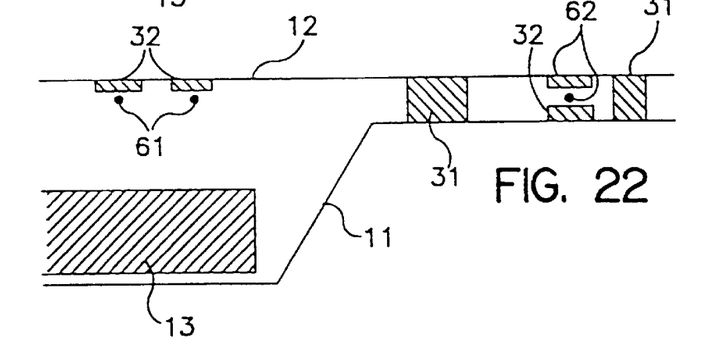

An absorbent article shown in FIG. 22 is different from that shown in FIG. 21 in that the topsheet 12 comprises a single member secured to backsheet 11 by adhesive 31.

Figure 23:
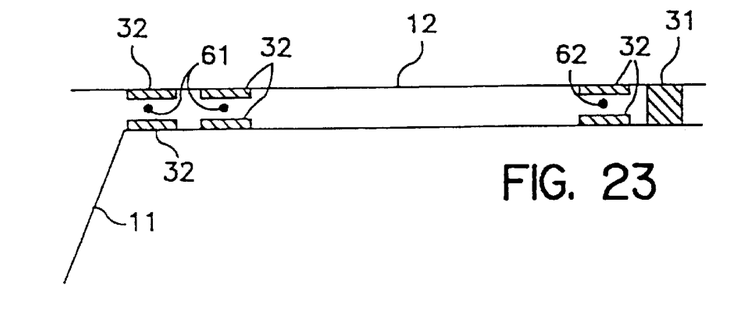

Alternatively, as shown in FIG. 23, all the elastic members 61 and 62 may be arranged between the backsheet 11 and topsheet 12 and connected thereto by adhesive layers 32.

As described above, the absorbent article of the present invention comprises a topsheet which includes communicating means in the crotch region of the article, and elastic members for forming the leg gathers disposed to extend along the periphery of the communicating means. The communicating means serves as the inlet of the pocket defined between the topsheet and the backsheet for receiving urine and fecal material. This provides comfort to the wearer during use. Since the elastic members for forming the leg gathers are disposed to extend along the periphery of the communicating means, the improved positional and shape stabilities of the communicating means are obtained.

The elastic members which form the leg gathers are disposed to extend primarily around the leg holes, and are not located in the crotch region where the elastic members are not required to be present. Accordingly, the absorbent article has softness and flexibility, and provides a snug fit and comfort to the wearer during use, with its leg gathers effectively preventing leakage from the article. Furthermore, as the elastic members are not bonded to the backsheet, the backsheet is not gathered or corrugated by the elastic members. This helps provide the article with a good appearance in its crotch region of the absorbent article.

We claim:

1. An absorbent article comprising:

a waist hole, first and second leg holes, and a crotch region defined between said leg holes;

a topsheet facing toward a wearer's body;

a backsheet disposed outwardly of the topsheet away from the wearer's body;

an absorbent core interposed between the topsheet and the backsheet;

a communicating means for permitting bodily waste to pass therethrough, said communicating means positioned so that at least a portion thereof extends into the crotch region, said communicating means comprising a first through aperture extending through the topsheet in a front portion of the crotch region and a second through aperture extending through the topsheet in a rear portion of the crotch region;

a first elastic member forming substantially one half of a first leg gather on the first leg hole and one half of a second leg gather on the second leg hole; and a second elastic member forming substantially a second half of the first leg gather on the first leg hole and substantially a second half of the second leg gather on the second leg hole, the first and second elastic members together defining the first and second leg gathers;

wherein the first elastic member extends around substantially one half of the periphery of the first aperture; and wherein the second elastic member extends around substantially a second half of the periphery of the second aperture, the first and second elastic members together encircling the communicating means.

2. The absorbent article of claim 1, further comprising:

a third elastic member and a fourth elastic member, said third elastic member forming along with said first elastic member substantially one-half of a first leg gather on the first leg hole and one-half of a second leg gather on the second leg hole, and said fourth elastic member forming along with said second elastic member a second half of a first leg gather on the first leg hole and a second half of the second leg gather on the second leg hole; wherein said third and said fourth elastic members extend between the first and second through apertures of the communicating means.

3. The absorbent article of claim 1, wherein the first and second through apertures are of different sizes.

4. The absorbent article of claim 1, wherein at least one of said through apertures includes a number of slits disposed in a substantially circular area adjacent edges of the crotch region and extend through the topsheet.

5. The absorbent article of claim 1, wherein said second through aperture extends through the topsheet material and said first through aperture comprises a plurality of slits formed in and extending through the topsheet material.

6. The absorbent article of claim 1, said topsheet comprising a dual-layered sheet material.

7. The absorbent article of claim 6, wherein
said first and second elastic members are interposed and secured between the dual-layered sheet material.

8. The absorbent article of claim 1, said second through aperture including a central portion thereof which is adhesively attached to said absorbent core, said second through aperture tapered in the direction of said absorbent core.

9. An absorbent article comprising:
a waist hole and first and second leg holes, each leg hole having a first end and a second end, and a crotch region defined between said first and second leg holes;
a topsheet facing toward a wearer's body;
a backsheet disposed outwardly of the topsheet and facing away from a wearer's body;
an absorbent core interposed between said topsheet and said backsheet;
the topsheet having front and rear portions with a first aperture formed in the front portion and having a first size for permitting urine to pass therethrough to the absorbent core and a second aperture formed in the rear portion of a size for permitting fecal material to pass therethrough to the absorbent core;
a first elastic member forming substantially one-half of a leg gather on the first leg hole and one half of a leg gather on the second leg hole; and
a second elastic member forming a second half of the leg gather on the first leg hole and a second half of the leg gather on the second leg hole, the first and second elastic members together defining the first and second leg gathers;
wherein the first elastic extends around substantially one half of the periphery of the first aperture; and
wherein the second elastic member extends around substantially a second half of the periphery of the second aperture, the first and second elastic members together encircling said first and second apertures.

10. The absorbent article of claim 9, wherein said first and second through apertures are of different sizes.

11. The absorbent article of the claim 10, wherein the size of the first aperture is less than the size of the second aperture.

12. The absorbent article of claim 9, further comprising:
a third elastic member and a fourth elastic member, said third elastic member forming along with said first elastic member substantially one-half of a first leg gather on the first leg hole and one-half of a second leg gather on the second leg hole, and said fourth elastic member forming along with said second elastic member a second half of a first leg gather on the first leg hole and a second half of the second leg gather on the second leg hole; wherein
said third and said fourth elastic members extend between the first and second through apertures of the communicating means.

13. The absorbent article of claim 9, wherein the first aperture includes a plurality of slits in the topsheet.

14. The absorbent article of claim 9, wherein the top sheet comprises a dual-layered sheet material.

15. The absorbent article of claim 14, said first and second elastic members interposed and secured between the dual sheet material.

16. The absorbent article of claim 9, said topsheet attached to said absorbent core in said first aperture.

17. The absorbent article of claim 16, further comprising a plurality of concentric slits formed in said first aperture.

18. The absorbent article of claim 17, wherein said first aperture tapers as it approaches the absorbent core.

19. An absorbent article comprising:
a main body having a waist hole, first and second leg holes, and a crotch region, said main body comprising a topsheet facing toward a wearer's body, a backsheet disposed outwardly of the topsheet, and an absorbent core interposed between the topsheet and the backsheet;
the topsheet defining a first aperture for permitting urine to pass therethrough in a first region of the crotch region to the absorbent core and a second aperture for permitting fecal material to pass therethrough in a second region of the crotch region to the absorbent core;
a first elastic member extending along a periphery of a first leg hole from a first end thereof to a midpoint thereof, continuously extending therefrom along one portion of the periphery of the first aperture to a midpoint of a second leg hole, and further extending therefrom to a first end of the second leg hole so that the first elastic member is disposed in a substantially U-shaped configuration; and
a second elastic member extending along a periphery of a first leg hole from a second end thereof to a midpoint thereof, continuously extending therefrom along a portion of the periphery of the second aperture to a midpoint of the second leg hole; and further extending therefrom to a second end of the second leg hole so that the second elastic member is disposed in a substantially U-shaped configuration which is inverted relative to the first U-shaped configuration, the first and second elastic members together encircling said first and second apertures.

* * * * *